United States Patent [19]

Tomei et al.

[11] Patent Number: 4,758,727

[45] Date of Patent: Jul. 19, 1988

[54] METHOD AND APPARATUS FOR THE MEASUREMENT OF LOW-LEVEL LASER-INDUCED FLUORESCENCE

[75] Inventors: L. David Tomei, Dublin; Fred Cornhill, Worthington; Jogikal Jagadeesh; Michael Boninger, both of Columbus, all of Ohio

[73] Assignee: Ohio State University Research Foundation, Columbus, Ohio

[21] Appl. No.: 828,694

[22] Filed: Feb. 12, 1986

[51] Int. Cl.$^4$ .............................................. G01J 3/10
[52] U.S. Cl. ............................. 250/458.1; 250/461.2
[58] Field of Search ............... 250/458.1, 459.1, 461.2, 250/461.1; 350/96.27, 527

[56] References Cited

U.S. PATENT DOCUMENTS

| | | |
|---|---|---|
| 3,450,455 | 6/1969 | Landre. |
| 3,516,746 | 6/1970 | Shibata et al. |
| 3,981,590 | 9/1976 | Perkins. |
| 4,107,534 | 8/1978 | Piltingsrud ........................ 250/368 |
| 4,523,799 | 6/1985 | Delhaye et al. ................... 350/527 |

FOREIGN PATENT DOCUMENTS

| | | | |
|---|---|---|---|
| 0123942 | 11/1984 | European Pat. Off. | ......... 250/327.2 |
| 0155813 | 9/1985 | European Pat. Off. | ............. 250/368 |

OTHER PUBLICATIONS

Bussini et al, "A Silicon Rubber Scint. Comp. . . . for Rad. Det.", Nucl. Inst. & Methods 107, #2, (1973) p. 333.
Nicoll, F., "Mural T.V. Display using Fiber Optics", RCA Technical Notes (RCA TN No.:188); (1958).
Dyer et al, "Vidicon Microscope for Count. Fluorescent Particles", Rev. of Scient. Instru., vol. 42, #4, (1971) p. 508.
"The FACS Analyzer Fluorescence and Volume Cell Analysis" brochure, Becton and Dickenson FACS Systems, 1982.
"The New FACS 400 Series, FACS 440, FACS 420, FACS 400, Fluorescence Activated Cell Sorting" brochure, Becton Dickenson FACS Systems, 1981.
"Photodigitizing with PDS Microdensitometer Systems" brochure, Perkin-Elmer not dated.
"Microdensitometer 3CS" brochure, Joyce-Loebl, not dated.
"Microdensitometer 6" brochure, Jouce-Loebl, not dated.
"EIKONIX ® Applied Research Software and Product Development Feasibility and Impact Studies Automated Instruments" brochure, EIKONIX ® Corp., not dated.
"ACAS 470 Workstation" Brochure, Meridian Instruments, Inc., not dated.

Primary Examiner—Janice A. Howell
Assistant Examiner—Richard Hanig
Attorney, Agent, or Firm—Emch, Schaffer, Schaub & Porcello Co.

[57] ABSTRACT

A method and apparatus for measuring low-level laser-induced fluorescence are disclosed. A laser is used to produce a coherent beam of light which is sequentially passed through a beam expander, iris diaphram, focusing lens and three-dimensional scanner before being focused onto a rigidly mounted target. A computer is used to predeterminately control the pattern and the rate at which the scanner passes the beam of light over the target. The light transmitted onto the target induces fluorescent light in the target. The fluorescent light is sequentially gathered by a biased cut optical fiber member and directed into a photomultiplier tube where the intensity of the fluorescent light is measured. The intensity data is then digitized and recorded by the computer as a function of the coordinates of each preprogrammed point location of the beam impinging upon the target. This data is used to produce an image of all or a portion of the target on a visual monitor. In addition, the data can be recalled and used for further analysis of the target.

26 Claims, 14 Drawing Sheets

α = BIAS CUT ON TAPER

β = DEFLECTED ACCEPTANCE ANGLE

θ = ACCEPTANCE ANGLE OF FIBER
   (NUMERICAL APERTURE APPROX. 0.7)

METHOD AND APPARATUS FOR THE MEASUREMENT OF LOW-LEVEL LASER-INDUCED FLUORESCENCE

BACKGROUND OF THE INVENTION

The present invention relates a method and apparatus for the measurement of low-level laser-induced fluorescence in the field of cytofluorometry. Cytofluorometry has been greatly enhanced with the development of fluorescence dyes that are specific for deoxyribonucleic acid (DNA). These dyes permit the determination of the ratios of total DNA present in a cell population and, since the total amount of DNA doubles as a cell progresses through its proliferation cycle, the distribution of cell cycle positions that existed in a cell population is easily determined statistically. This is based upon the fact that, within necessary tolerances, the amount of dye bound to a cell is directly proportional to the amount of DNA present.

Fluorescence is the emission of light whose wavelength is different from that used to induce or excite the molecule of dye. Therefore, common fluorescence techniques require that the dye bind specifically to some component which is to be measured such as DNA. Such specificity is obtained by structurally modifying the dye molecule or coupling a dye molecule to another molecule that has the required specificity of binding. Another technique which utilizes fluorescence emission is based upon other properties of some dye molecules. When these molecules are in an aqueous environment, their fluorescense characteristics are distinctly different from that obtained in a hydrophobic environment. Since all biological membrances have hydrophobic regions, the amount and kind of fluorescence obtained following staining is related to the structural state of that membrane.

Several analytical techniques have been developed which exploit these various properties of fluorescent dyes. These techniques include photo-bleaching, fluorescence quenching, and shifts in fluorescence emission spectra. Problems are continuously encountered with these various techniques in that total fluorescence per cell, following any general technique with any particular dye, varies markedly and the variation is not quantitated for the expressed purpose of defining the degree or nature of cell cooperativity in a coordinating, interacting, cell mass.

Another fluorescence technique, stereological computer assisted cytofluorometry (SCAC) provides for the measurement of laser-induced cellular fluorescence in a cell or tissue mass (e.g. monolayer cell cultures or tissue sections). Dependent upon the nature of the fluorescent dye employed, the cellular response-density distribution profile will provide data of profound theoretical as well as practical significance. SCAC provides a technique for the quantitation of cell behavior and responses to drugs within the context of the cell mass or tissue. This has led to the development of new pharmacological parameters and is expected to lead to more refined and sophisticated parameters with which to study drug actions in the fields of cancer diagnosis, chemoprevention and chemotherapy, environmental and forensic toxicology, as well as basic biological sciences.

Currently there are two basic apparatuses for performing cytofluorometric studies. A fluorescence microscope such as the FACS TM series analyzer manufactured by Becton Dickinson provides observation of cells contained in a culture dish. The fluorescence microscope is highly accurate when analyzing a small area but cannot measure cell groupings larger than a culture dish without destroying the spatial relationship of the cells. The second apparatus, a Flow Cytometer is designed to provide observation for a large number of cells, but the cells must be in suspension, thereby eliminating any possibility of obtaining spatial data. The CYTOFLUOROGRAF system from the Ortho Instruments Corporation is an example of a flow cytometer. The flow cytometer provides highly accurate information on the frequency distribution of fluorescence intensity in a randomly dispersed cell populations. However, no information is provided regarding the spatial relationship that may exist between cells in the tissue, tumor or culture prior to dispersal and staining.

Interpretation of frequency distributions of fluorescence intensity is seriously hampered by the fact that the response of the original cell population is rarely spatially homogenous. Heterogeneity of cell identity, morphology and drug responsiveness is commonly observed but not considered in current cytofluorometric analytic techniques. However, population heterogeneity is regarded by biologists as being an inherent quality of coordinating cell populations found in all animal tissues, tumors, primary cell cultures, and in rudimentary form, laboratory cell lines. The present invention, method and apparation, provides the ability to observe large areas of tissue, while maintaining full spatial relationships without the need for any special preparation.

SUMMARY OF THE INVENTION

The present invention relates a method and apparatus capable of rapid wide-field scanning of low-level laser induced flourescence of tissue sections, cell cultures, and other biological materials, while maintaining high spatial resolution. The method and apparatus of the present invention measures off-axis fluorescence. The fluorescence measurements permits full digitalization of images with 16 bit precision for $2-4 \times 10^6$ pixels. The target areas scanned are greater than 25 cm$^2$ with a resolution of 5–10 $\mu$m and the scanning time is between 1 and 6 seconds dependent upon computer processing and storage limitations. The SCAC methodology, provides for the acqustion of information from a large number of individual cells as does flow cytofluorometry. However, in addition to individual cell responses, the present invention will provide highly accurate information regarding the spatial distribution of those cells within the total population. This is of particular importance in the areas of tumor biology, pathology and early detection of abnormal cells in tissues and organs. The SCAC design of the present invention provides for analysis of large cell numbers in vitro with high spatial precision.

The apparatus of the present invention incorporates an optical fiber taper for high efficiency light gathering and transmission to a highly sensitive detector. The properties of the fibers can be exploited to shift the detector off-axis. This apparatus of the present invention makes use of two fiber properties: tapered fiber transmission and biased cut deflection. Further, extramural absorption material are added to provide further attenuation of off-axis incident laser light. The method and apparatus of the present invention will be further understood by the following description of the preferred embodiment with reference to the following figures.

DETAILED DESCRIPTION OF THE PREFERRED EMBODIMENT

Figure 1:
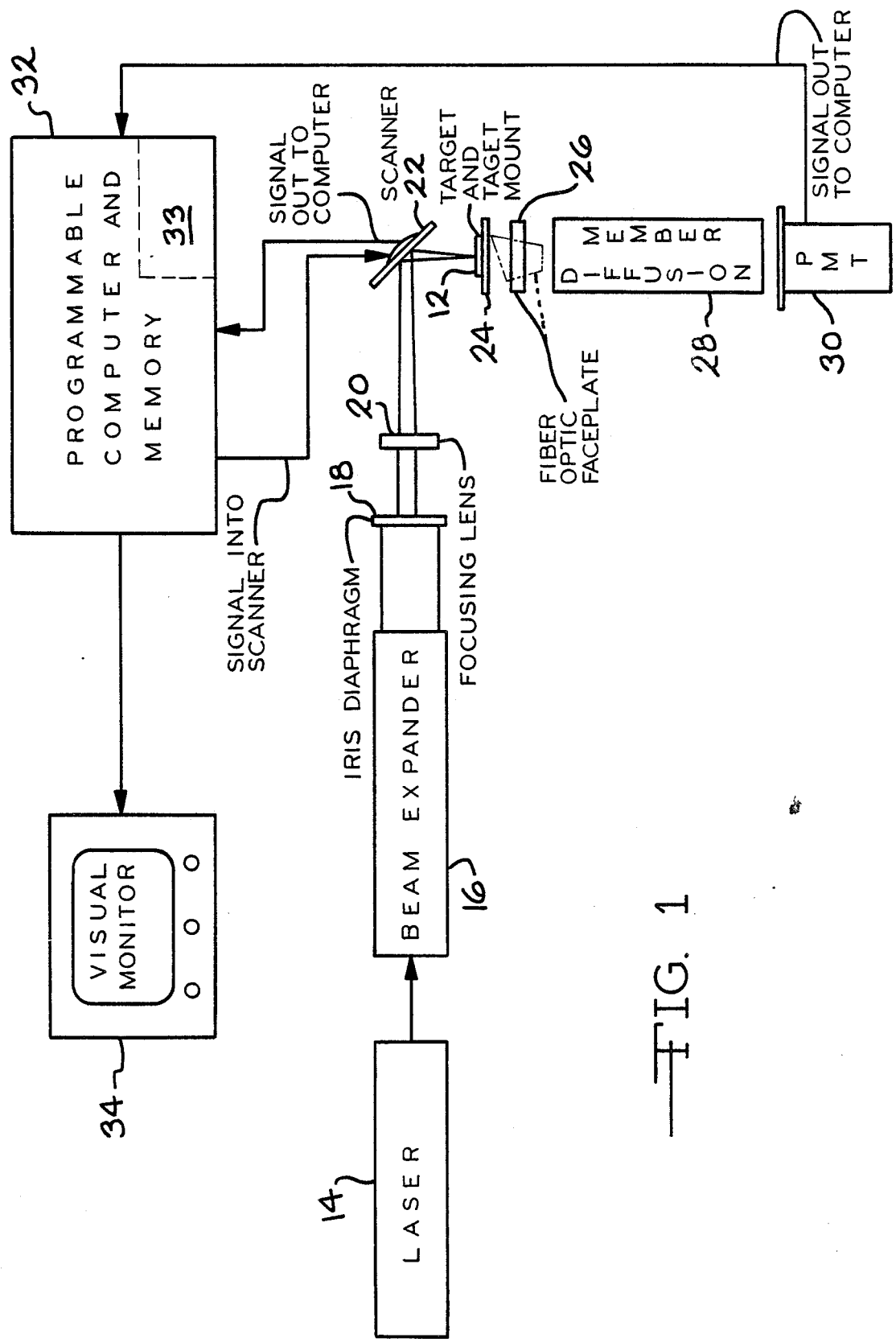
FIG. 1 is a block diagram of a scanning device according to the present invention.

The present invention relates to a method and apparatus for the off-axis detection of laser-induced fluorescence. Referring to FIG. 1, there is shown a block diagram of the components of a scanning device 10 according to the present invention. The scanning device 10 uses coherent light to scan a object or target 12. In the preferred embodiment, the components of the device 10 include; a tuneable laser 14, a beam expander 16, an iris diaphragm 18, a focusing lens 20, a three-dimensional scanner 22, a target mount 24, a fiber optic faceplate having a bias cut 26, a diffusion member 28, a photomultiplier tube 30, a programmable computer with memory 32 and a visual monitor 34. Together these components provide for rapid scanning of translucent targets to yield high resolution, wide-field fluorescence analyses of a large number of cells in vitro, with high spatial precision.

The means for generating the coherent beam of light is a laser 14. It is desirable that the laser 14, shown in FIG. 1 emit a coherent polarized beam of light 15 having a wavelength in the range of 350 to 540 nanometers. The light beam 15 exiting the laser 14 is approximately 1 millimeter in width, which is too small to be used effectively by the reflecting mirrors within the scanner 22. Therefore, the present invention provides a beam expander 16 which receives the laser beam 15 and enlarges the size of the beam 15 to ensure utilization of the greatest possible surface area of the reflecting mirrors within the scanner 22. The preferred beam expander 16, as shown in FIG. 1, is a Buschnell variable beam expander having a magnification power range of 9× to 30×. In the preferred embodiment, the beam expander 16 is adjustable to expand the beam size through a range from 1 millimeter to 10 millimeters.

As an alternative to the use of a variable beam expander, a single power beam expander may also be used with Applicant's invention. In such cases an iris diaphragm 18 is included to receive the expanded beam 15 from the single power beam expander. The iris diaphragm 18, also known as a field iris, is intended to vary the diameter of the beam 15 input to the focusing lens 20 and the scanner 22, thus varying the spot size on the target 12. Consequently, the iris diaphragm 18 is used to more finely tune the size of the beam of light 15.

Referring now to FIG. 1, the beam of light 15 exiting the beam expander 16 or iris diaphragm 18 is passed through the focusing lens 20 which focuses the beam of light 15 on the target 12. Together, the beam expander 16/iris diaphragm 18 and focusing lens 20 permit the beam of light to be focused to a spot of predetermined dimension at the target plane of the translucent target 12.

In the preferred embodiment, the light received by the focusing lens 20 is a gaussian columnated coherent beam of light. Using this assumption, the final spot size upon the target 12 is diffraction limited and governed by the following equation:

$$d = 4F\lambda/\pi D, \quad (1)$$

wherein
d = spot size
F = focal length of focusing lens
λ = wavelength of the light
D = aperture of input beam to focusing lens According to equation (1), the proper selection of the focal length (F) of the focusing lens 20, the wavelength (λ) of the coherent light beam 15, and the aperture (D) of the input beam to the focusing lens 20, will allow for the size of the beam spot (d) on the target 12 to be varied as desired. The smallest available spot size is approximately one micron. Thus, the present invention is capable of scanning at a variety of intervals with the smallest being a one micron interval.

The focused beam of light 15 exiting the focusing lens 20 is received by the three-dimensional scanner 22 which operates to control the passing of the light beam 15 over the target 12. The scanner 22 as shown in FIG. 1 is manufactured by General Scanning, Inc. and uses computer controlled mirrors to pass the focused beam of light 15 back and forth across the target 12. The scanner 22 is capable of scanning an area of any size, up to 20 millimeters by 40 millimeters, while operating at a raster rate of up to 20 Hz or a vector rate of up to 280 mm/sec. Computer controlled drive motors cause the mirrors of the scanner 22 to move such that the scanner 22 has accurate X and Y coordinate scanning capabilities with a simultaneous Z coordinate correction to yeild a beam of light 15 with a flat field of focus. If desired, the Z coordinate of the scanner 22 can be programmed to coordinate with an uneven topographical field of focus on the target 12.

The scanner 22 passes the focused coherent beam of light to the target 12, thereby inducing fluorescence in a predetermined pattern and at a predetermined rate set by the computer 32 so that data is obtained as to the intensity of the fluorescence at differing points on the target 12. At precise predetermined points during the scanning process, the intensity of the light is measured by the photomultiplier tube 30 and recorded by the computer 32 as a function of location of the beam 15 on the target 12. By taking successive point measurements of the intensity of the fluorescence and relating them back to the location data in the computer 32, the data is used to analyze the target 12 or recreate a visual image of the target 12 on a visual monitor 34.

Figure 2:
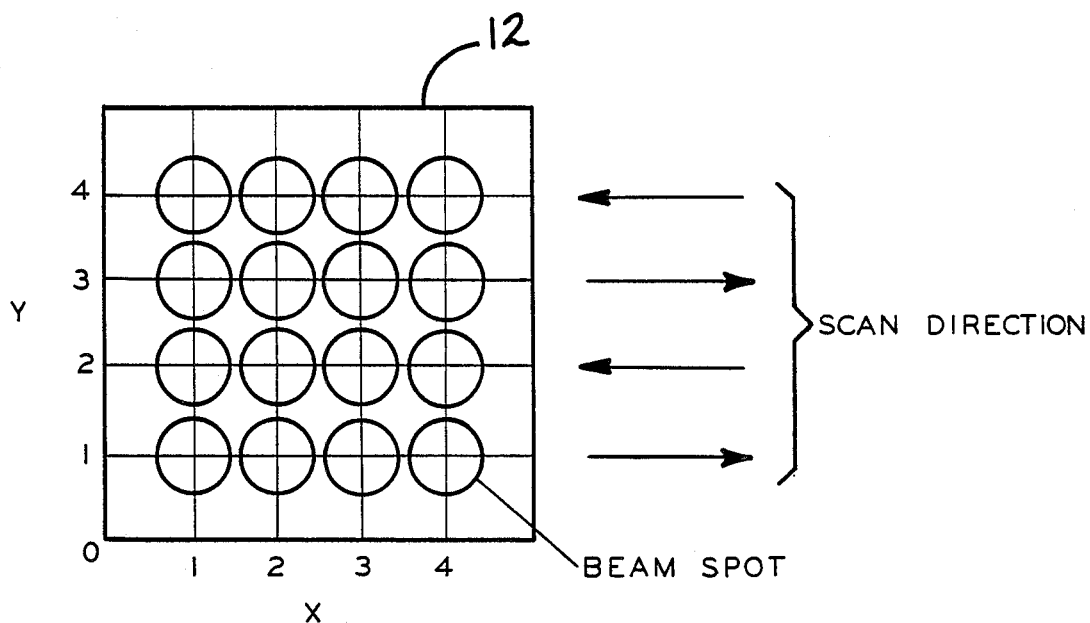
FIG. 2 is an exemplary view of a scanning pattern of a translucent object with a scanning device according to the present invention.
Figure 5:
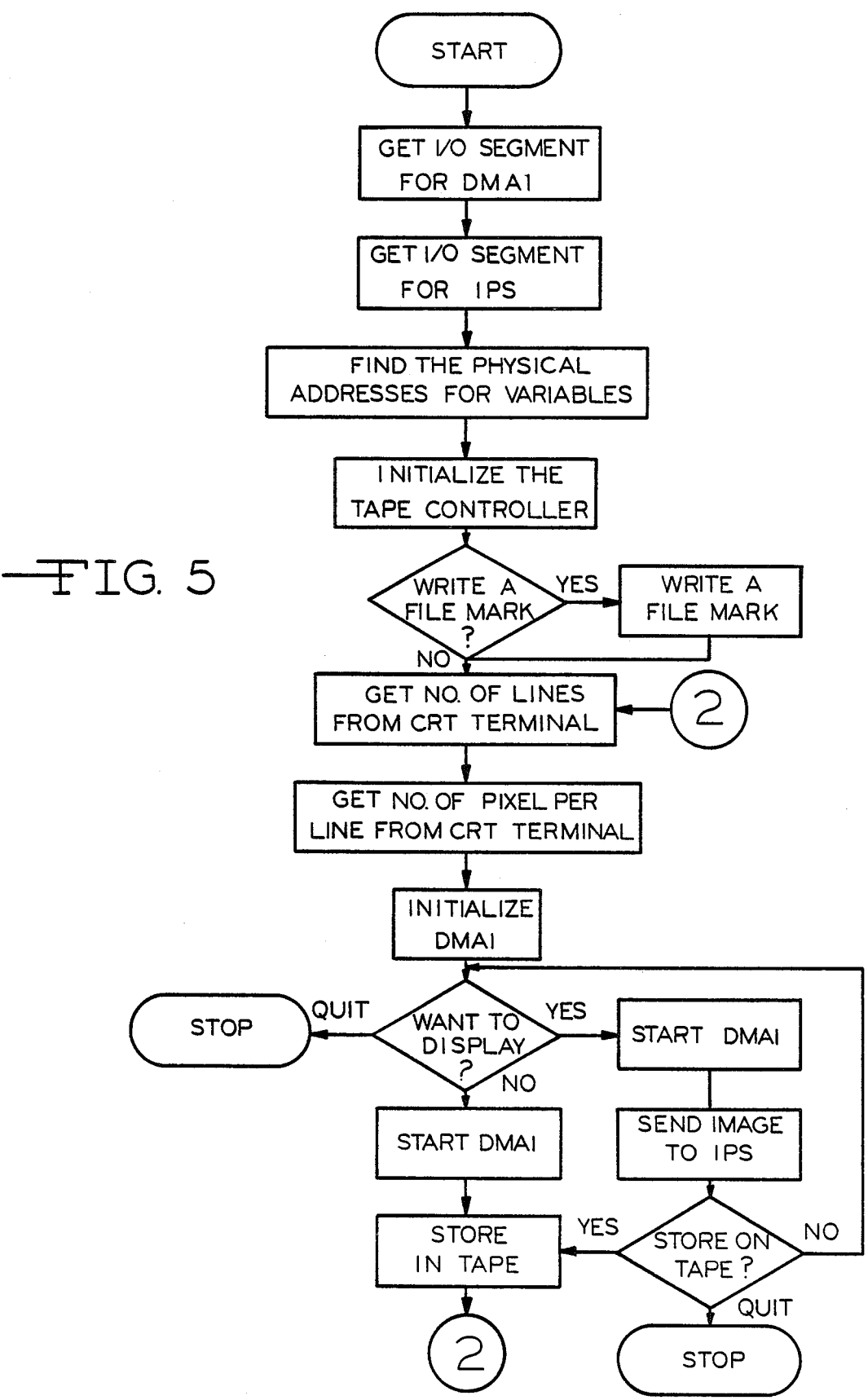
FIG. 5 is a flowchart representing the scanning program by which the present invention operates.

The target 12 is scanned over a very large series of points using a back and forth pattern as shown in FIG. 2. The X, Y coordinates and the rate of scanning are predetermined and programmed through the computer 32. The scanning program is individually drawn to the specifics of the application. The flowchart for the scanning program is shown in FIG. 5. At each scanning point, the fluorescence intensity is measured and recorded as a function of the X, Y coordinates of the beam. For example, the scanner 22 would be programmed to scan the target 12, as shown in FIG. 2, in a sequential pattern over the following (X,Y) coordinates: (1,1), (1,2), (1,3), (1,4), (2,4), (2,3), (2,2), (2,1), (3,1), (3,2), (3,3), (3,4), (4,4), (4,3), (4,2) and (4,1). The intensity of the fluorescence being excited at each of the scanning points is measured by the photmultiplier tube 30 in terms of analogue data. The analogue data for each scanning point is then digitized by the computer 32 and recorded as a function of the X, Y coordinates of that particular scanning point.

The present invention utilizes a three-dimensional scanner, such as that manufactured by General Scanning, Inc. The use of such a scanner provides in that the target mount 24 is stationary, thereby eliminating the wobble and jitter experienced with moving target mounts. Due to the minute size of the focused beam spot on the target 12 and the large amount of point data being taken, it is important that the target 12 be rigidly mounted in a fixed position on the target mount 24 to maintain the proper focusing, depth of field, and spot size.

Positioned directly below the target mount 24 and thus below the target 12 itself is a fiber optic faceplate 26 which is used in conjunction with a diffusion member 28 to increase the efficiency of the highly sensitive photomultiplier tube 30. The sensing surfaces of photomultiplier tubes are characteristically nonuniform. The fluorescent light transmitted by the target 12 is minute in the form of a narrow columnated beam. If this beam were received by the photomultiplier tube 30, variations in the recorded intensity of the beam would occur as a result of variations in the location at which the narrow columnated light beam strikes the sensing surface of the photomultiplier tube 30. Therefore, the present invention utilizes the fiber optic faceplate 26 to gather as much light as possible and the diffusion member 28 spreads the light beam broadly as possible to achieve full use of the photomultiplier tube 30.

Figure 4:
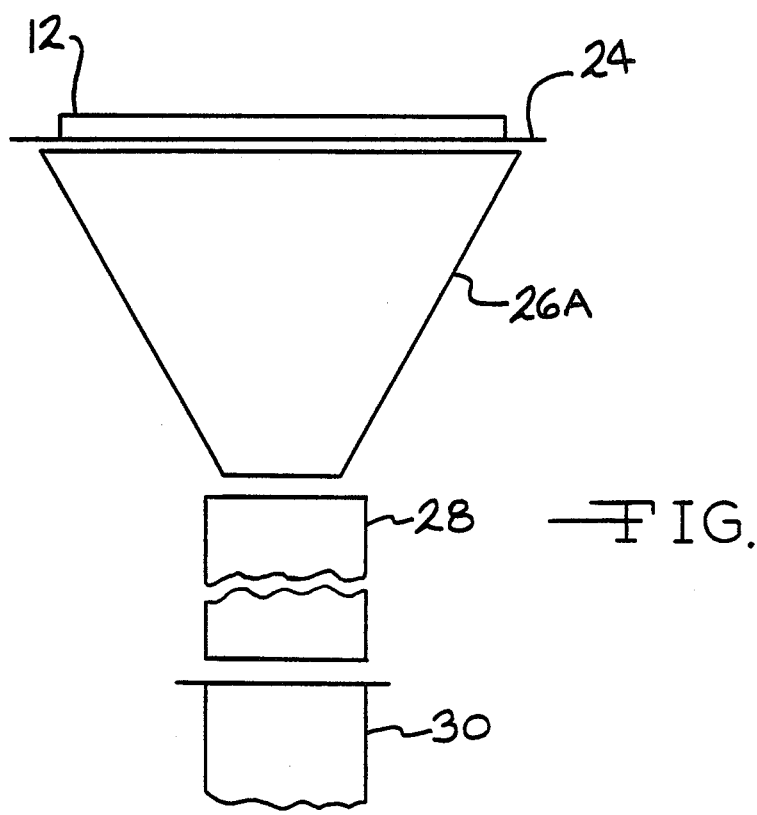
FIG. 4 is a block diagram showing an alternate embodiment of the fiber optic bundle as used with a scanning device according to the present invention.

One of two types of fiber optic faceplates 26 may be used with the present invention, depending upon the size of the window of the photomultiplier tube 30. When the window of the photomultiplier tube 30 is comparable in size to the target 12, then a flat disk-type faceplate, as shown in FIGS. 1 and 2, is used. When the scanning area of the target 12 is larger than the window of the photomultiplier tube 30, a tapered or frustoconical shaped fiber optic faceplate 26A, such as shown in FIG. 4, is used. The use of such fiber optic faceplates presents a marked improvement over prior art systems in which lenses are relied upon to gather and direct the light beam. The light gathering or flux-carrying capacity of the optical fibers within the taper 26A as used with the present invention is 10 to 70 times higher than that of standard optical lenses. The relative increase in light gathering capacity is numerically equal to the ratio of the squares of the numerical apertures. The effective numerical aperture of a typical lens capable of imaging a target area of at least several square millimeters is 0.10 to 0.20 as compared with optical fibers which have nominal numerical aperture values of greater than 0.60. Therefore, the use of optical fibers in conjunction with highly sensitive photomultiplier tubes 30 produces a marked advantage over instrument designs incorporating optical lens systems and/or solid-state light detectors.

Figure 6A:
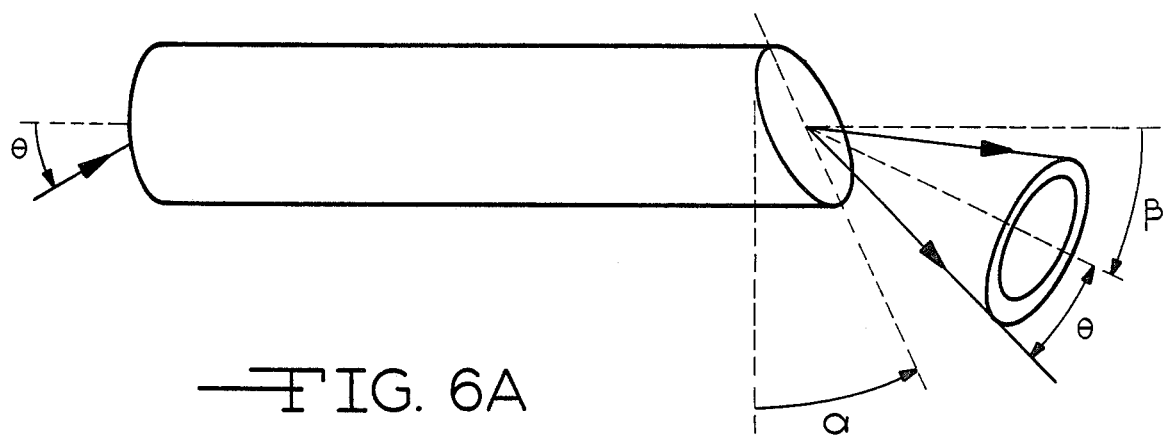
FIG. 6a is an exemplary view of a biased cut optical fiber faceplate.
Figure 6B:
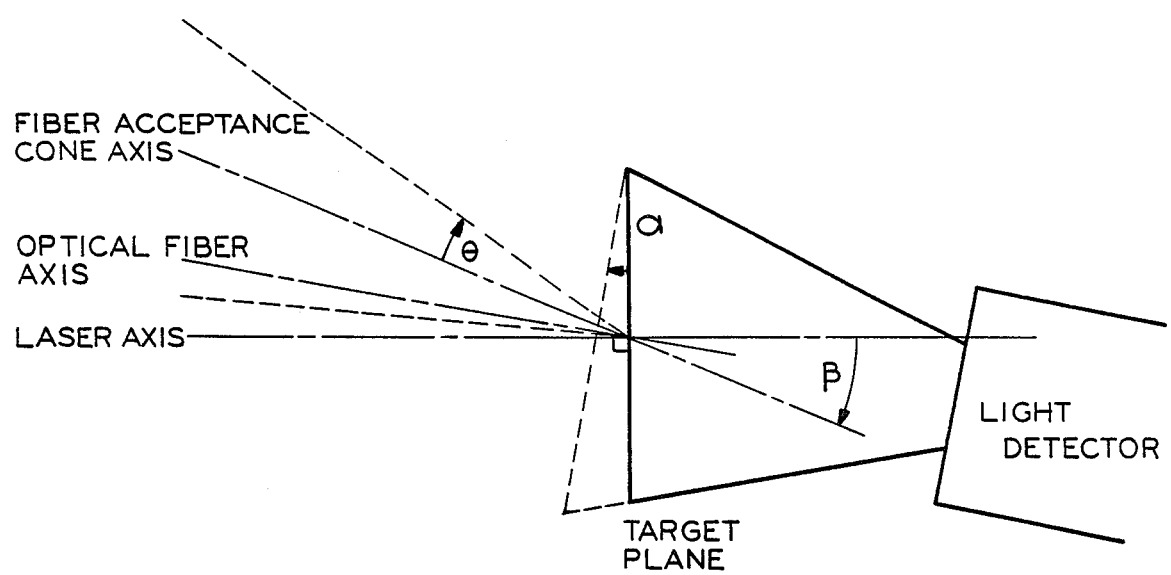
FIG. 6b is an exemplary view of a biased cut tapered optical fiber faceplate.

The fiber optic faceplate 26 is biased cut at a angle $\alpha$, preferably 30°. Referring to FIG. 6, the bias cut on the optical fiber faceplate 26 is shown as angle $\alpha$ and the acceptance angle of the fiber optic faceplate 26 is deflected by angle $\beta$. This provides a total deflection by angle $\beta$ or shift of the acceptance angle $\theta$ which comprises the acceptance cone of the fiber optic bundle. If laser light is shown onto a fiber outside of the acceptance cone, the amount of light transmitted along the length of the fiber will be severely limited. Thus, the present invention provides a fiber optic faceplate 26 having a bias cut such that light hitting perpendicular to the face of the fibers will not be in the acceptance cone. In this manner, a light source hitting perpendicular to the surface will be attenuated while excited fluorescence or scattered light may enter the acceptance cone. The bias cut fiber optic system of the present invention is capable of gathering 30% of the excited fluorescence from the target being scanned, as compared with current technology in which only 2% of the excited fluorescent light is gathered.

The optical fibers in the faceplate 26 also function as the first stage for light diffusion. Optical fibers will gather light from all angles within the acceptance cone. Upon exit from the faceplate 26 this light is rotated about a solid angle through which the intensity is uniformly distributed. This optic fiber property thus enhances the light scattering efficiency of the diffusion member 28.

Further attenuation of the light is accomplished by insertion of neutral density filters 27 between the fiber optic faceplate 26 and the diffusion member 28. In the preferred embodiment, a 620 nanometer filter is incorporated in order to eliminate the normal fluorescent room lighting, thus permitting operation of the instrument without extensive light protection. Further, a barrier filter (not shown) may be incorporated at this point to absorb light at the excitation wavelength while transmitting light at the fluorescent wavelength.

The diffusion member 28, shown in FIG. 1, is an open-ended hollow elongated member with a reflective interior surface. Such a member can be constructed of an open-end box using mirrored glass for the interior surface. Alternatively, milk glass may be used as the diffusion member 28. The primary functions of the diffusion member 28 are two-fold. First, the diffusion member 28 blocks out any remaining ambient light which will affect the intensity readings of the photomultiplier tube 30. Secondly, the diffusion member 28 allows the transmitted light to diffuse within its confines to more fully utilize the window of the photomultiplier tube 30 and thus yield more accurate results.

After the fluorescent light transmitted from the target 12 is directed to the photomultiplier tube 30 by the fiber optic faceplate 26 and diffusion member 28, the photomultiplier tube 30 detects and measures the fluorescence levels. The photomultiplier tube 30 is in turn linked to the computer 32 so that data obtained by the photomultiplier tube 30 regarding the intensity of the light is fed into the computer 32.

Once the device 10 is activated and scanning of the target 12 begins, the output of the photomultiplier tube 30 is sampled by the computer 32 as often as desired. The electrical signals relating the intensity of the fluorescent light are converted from analogue to digital values by the computer 32 for storage purposes. Using the preprogrammed position data and the stored intensity values, the computer 32 can provide a realtime pictorial reconstruction of the target 12 on a visual monitor 34. The capacity of the computer 32 to rapidly store the highly detailed data being viewed makes it possible to depict the entire area of the target 12 on the visual monitor as well as focus on particular points of interest by providing enlarged viewing of select portions of the target 12.

Figure 3:
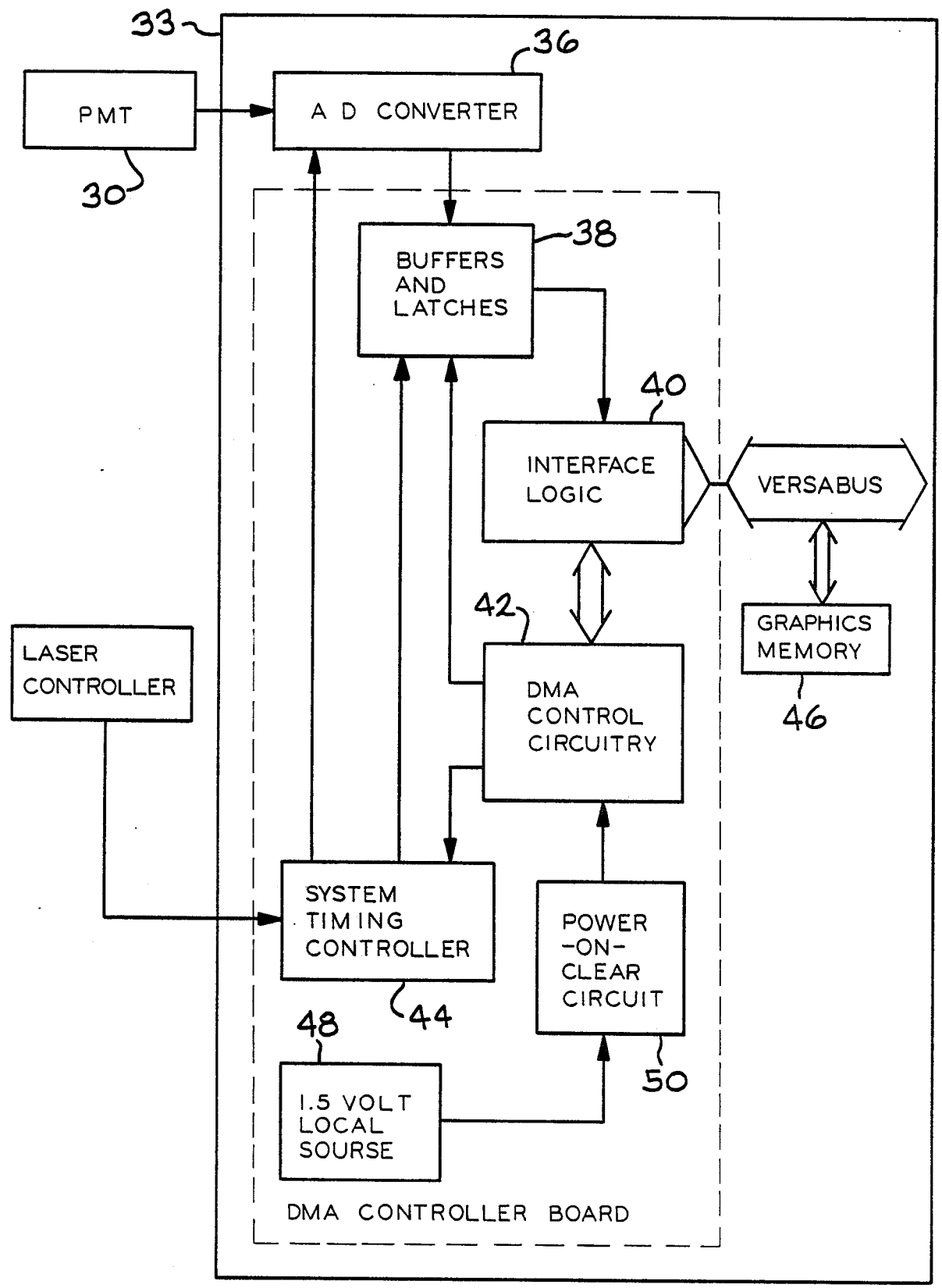
FIG. 3 is a block diagram of the electronic interface used to control the various components of a scanning device according to the present invention.
Figure 7:
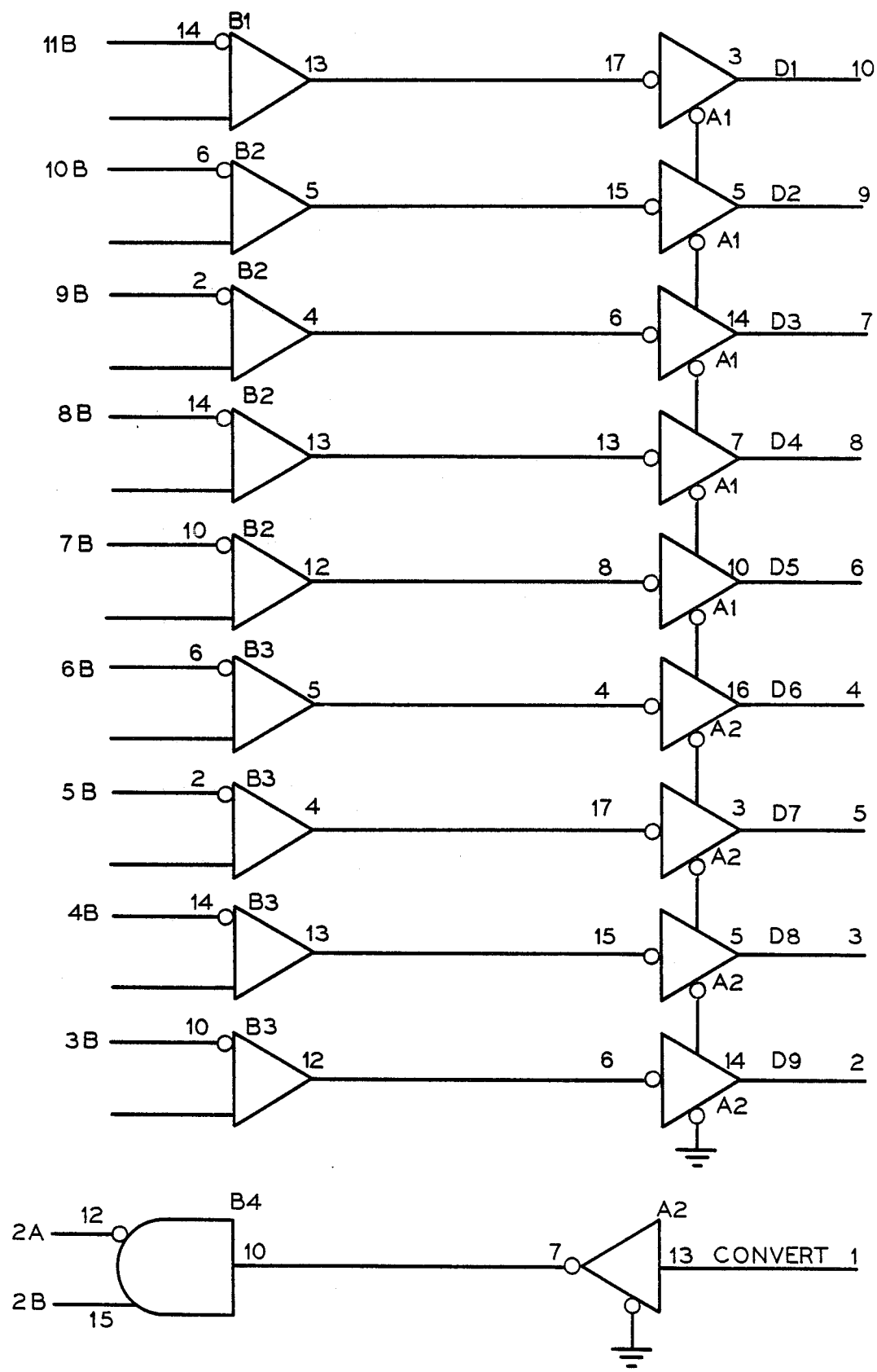
FIG. 7 is a schematic showing an analogue to digital convertor board as used in the present invention.
Figure 8:
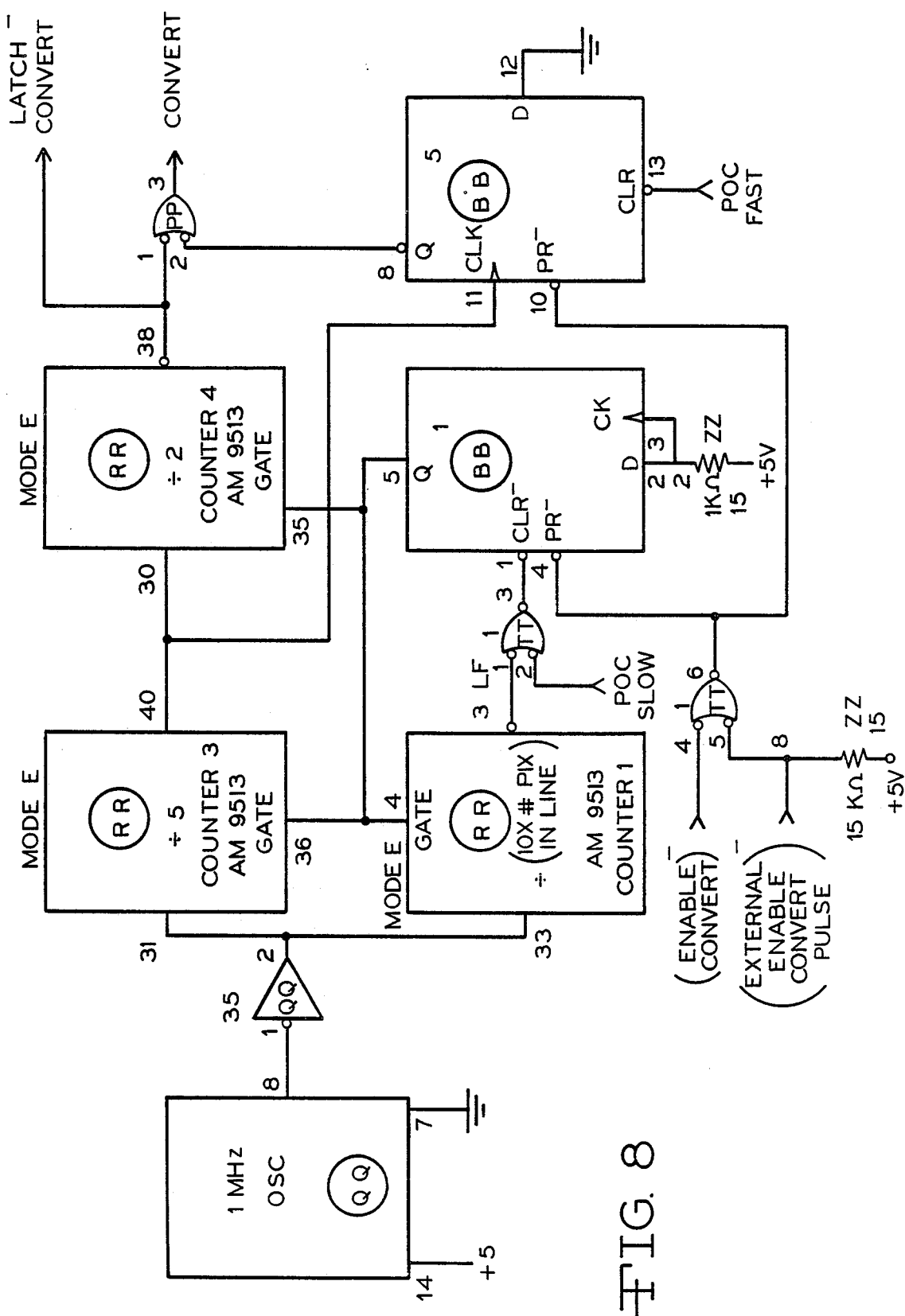
FIG. 8 is a schematic showing the clock circuitry as used in the present invention.
Figure 9:
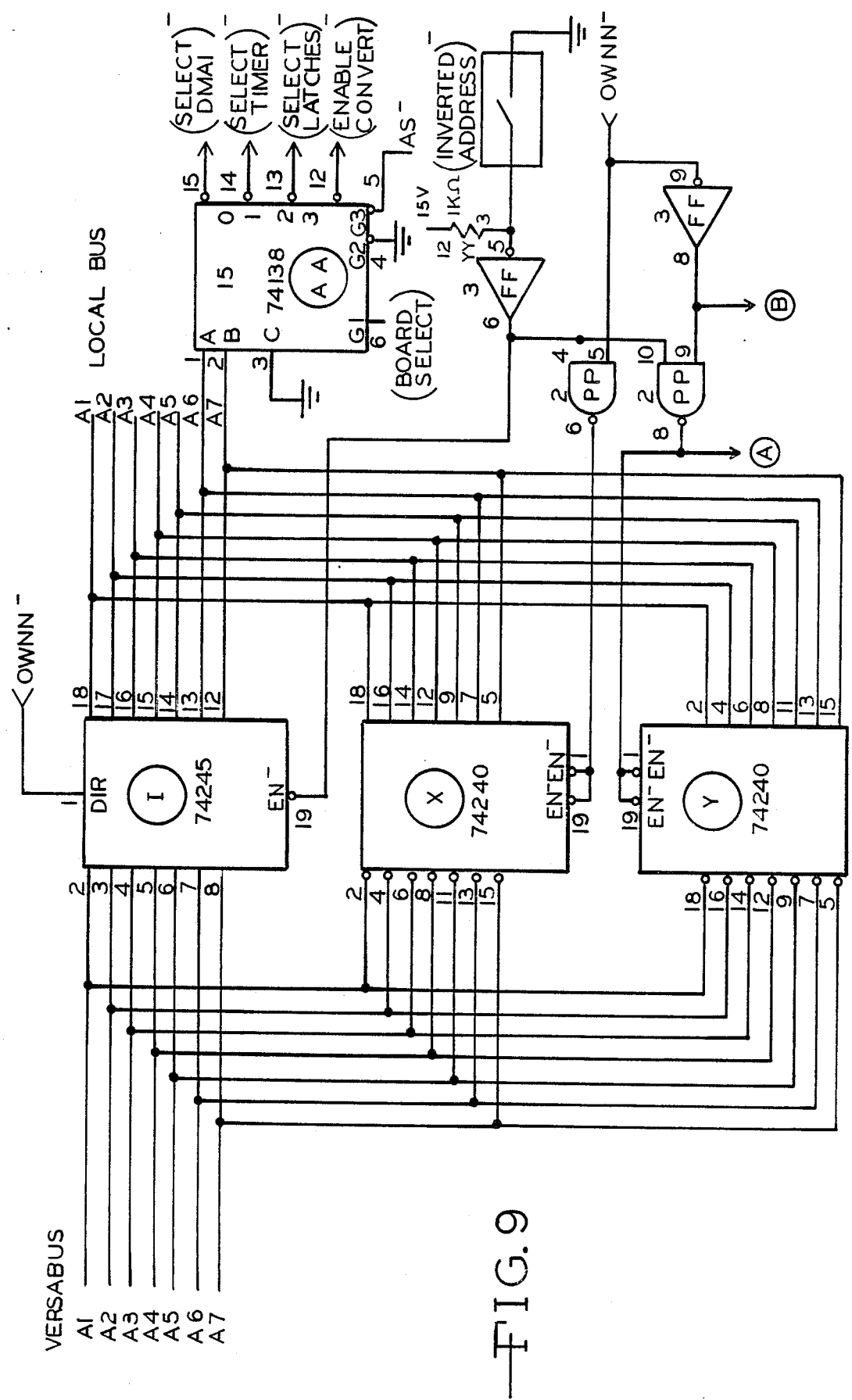
FIG. 9 is a schematic showing the low-order Address bus Interface circuitry as used in the present invention.
Figure 10A:
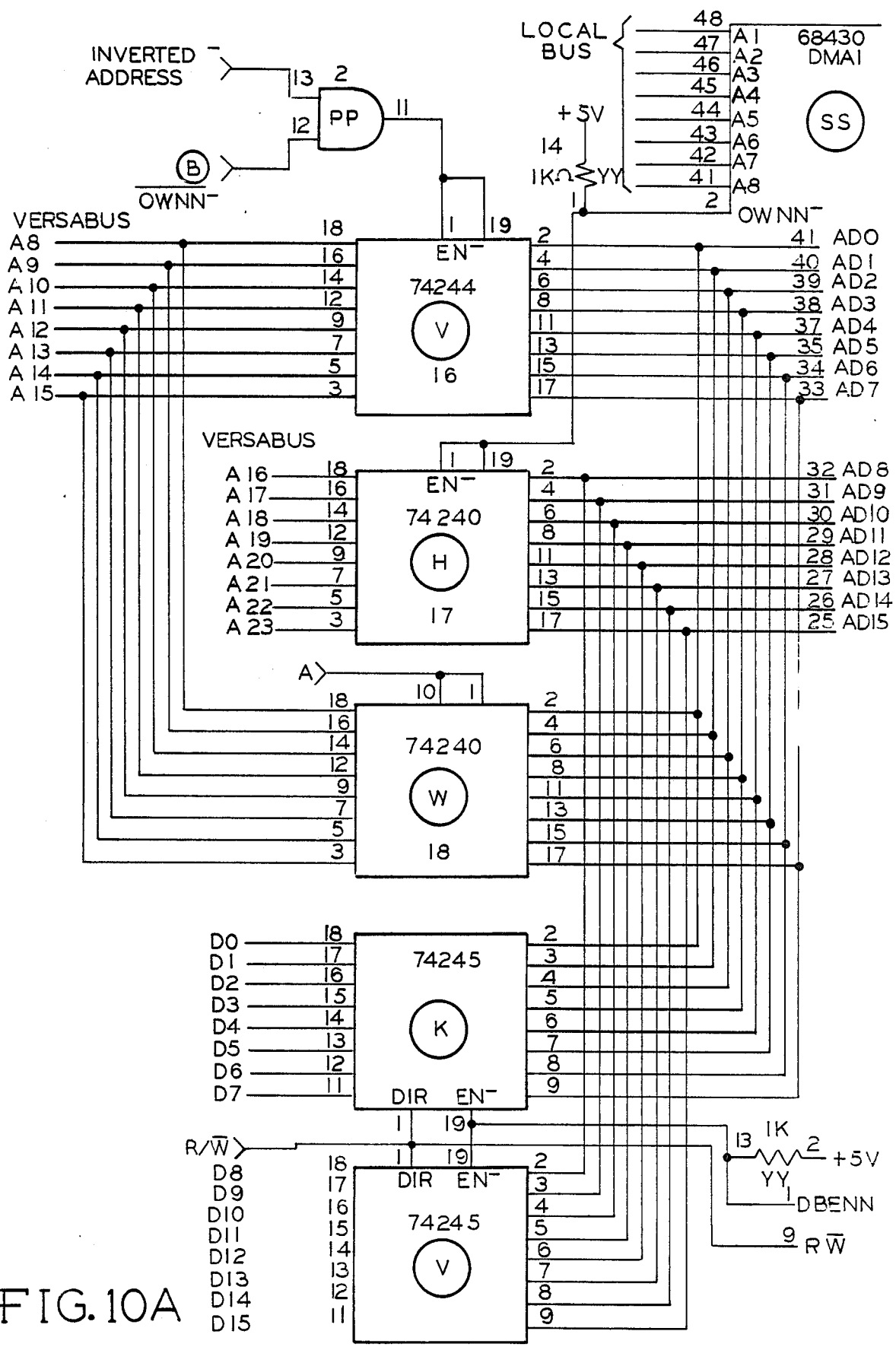
FIG. 10 is a schematic showing the DMA/Versabus Interface circuitry as used in the present invention.
Figure 10B:
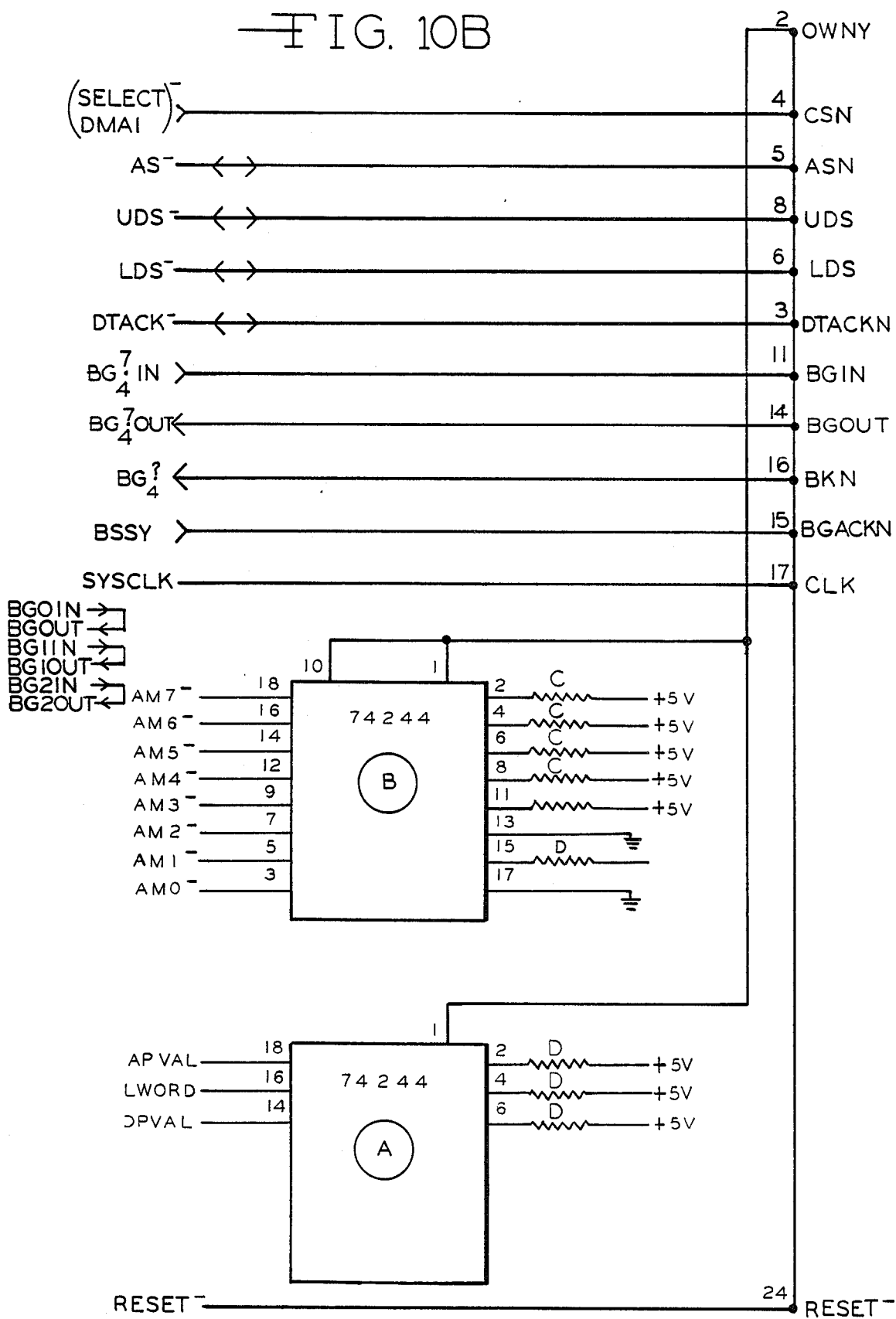
Figure 11:
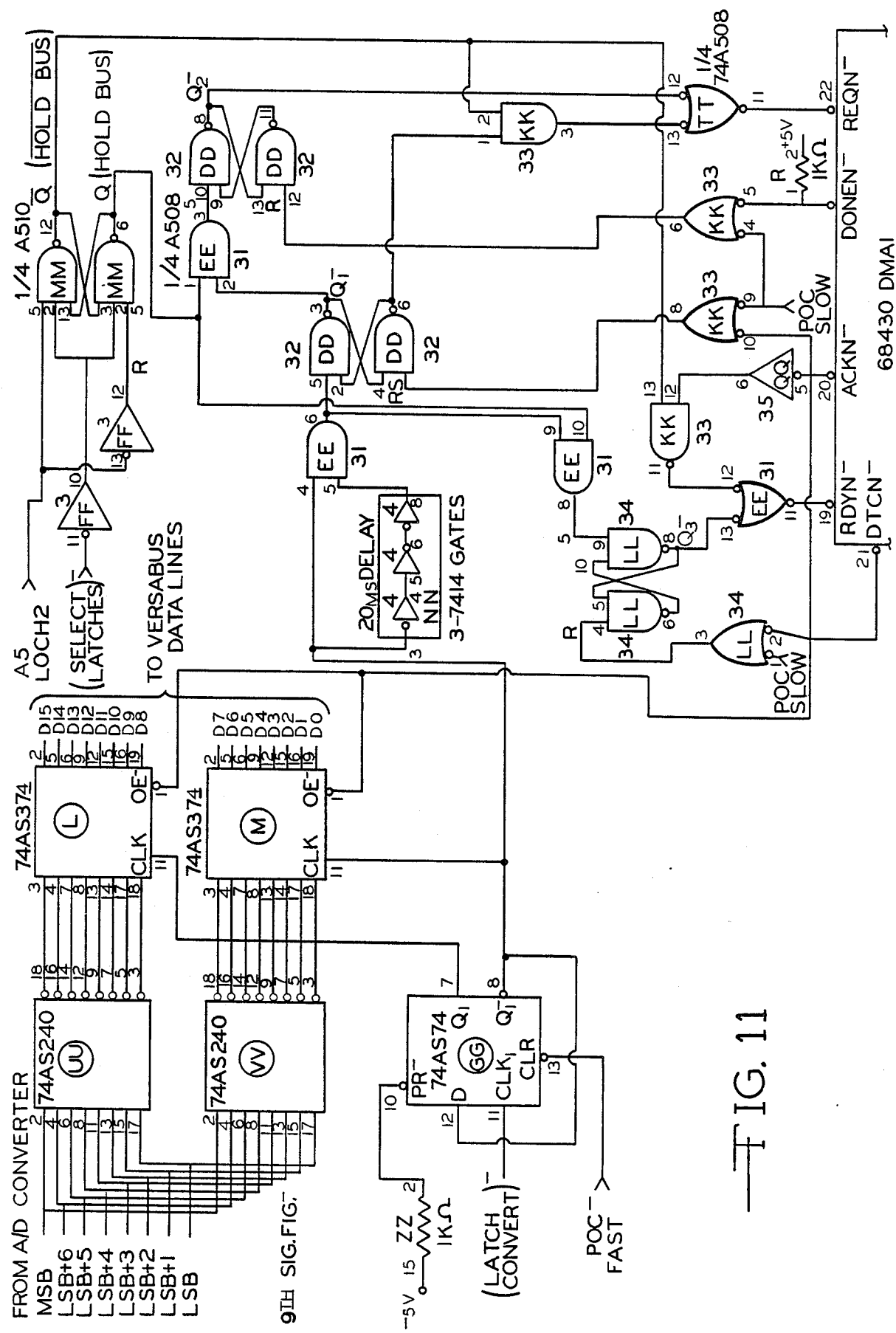
FIG. 11 is a schematic showing the DMA data path circuitry as used in the present invention.
Figure 12:
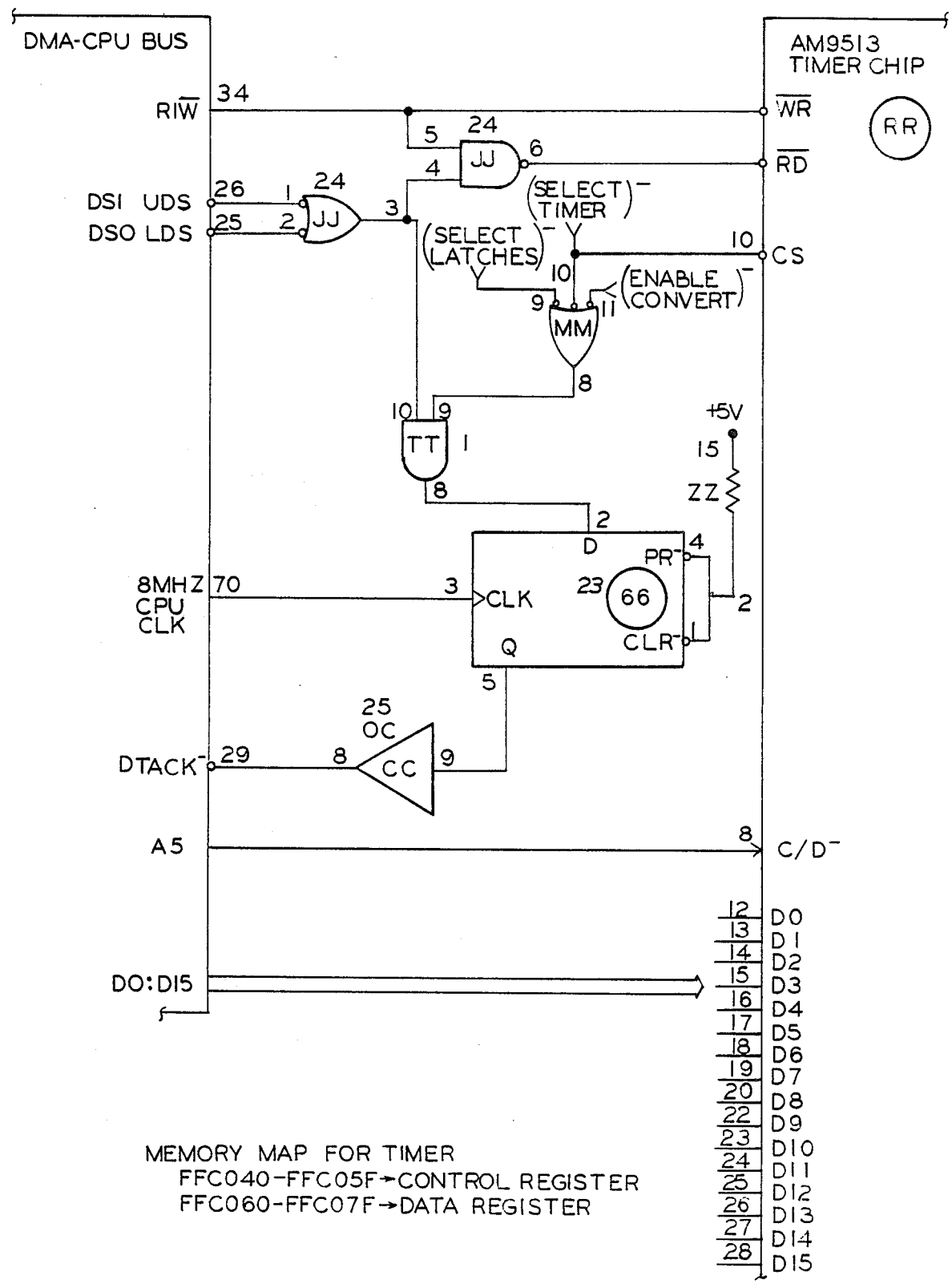
FIG. 12 is a schematic showing the timer interface circuitry as used in the present invention.

Referring now to FIG. 3, an interface is provided to collect the analogue intensity data output of the photomultiplier tube 30 and convert the data into digital form for the versabus-based computer 32. The interface 33 communicates with the computer 32 through direct memory access (DMA) with a minimum instantaneous transfer rate of 100,000 picture elements (pixels) per second. The interface 33 of the present invention is composed of five main subsystems including: an analogue-to-digital (A/D) converter 36 as shown in FIG. 7; a set of buffers and latches 38; bus interface logic 40 as shown in FIGS. 9, 10; a DMA controller 42 as shown in FIG. 11; and a system timing controller 44 as shown in FIG. 12. The DMA controller 42 and system timing controller 44 are used to properly operate the A/D converter 36, the set of buffers and latches 38 and the bus interface logic 40.

Referring now to FIG. 7, the A/D converter 36 transforms the image data signals which are received from the photomultiplier tube 30 into a digital form which is understandable by the host computer 32. The buffers change the voltage of the signals to a level which is compatible with the host computer 32 while the latches store the transformed data until it is efficient for the computer 32 to accept them.

Referring now to FIG. 11, the DMA controller 42 and the bus interface logic 40 of FIGS. 9 and 10 store and control information about the flow of the data to the computer 32 so that the computer 32 receives the data only when it is able to accept the information. The system timing controller 44 of FIG. 12 ensures that the proper number of pixels are placed into the memory 46 of the computer 32. In addition, the system timing controller 44 generates all the needed signals for the A/D converter 36.

Since the A/D converter 36 outputs emitter coupled logic (ECL) compatible singals, level shifters are required to provide transitor-transistor logic (TTL) signals. These signals are tied directly to a combination bus buffer/latch chip. The conversion timing is derived from a 1 MHz crystal feeding an AM9513 timing controller. It should be noted that higher frequency crystals may be used. The timing controller is started by means of an enable convert signal which can be generated by the host computer 32 under user control, or by a signal external to the board. The timing controller 44 generates the convert and latch signal, and also terminates its count automatically. The controller is completely software programmable.

The bus interface logic permits the use of both a positive true logic and negative true logic CPU bus. The bus also allows for a choice of an 8 or 16 MHz CPU clock speed. The board is memory-mapped, and may reside on any 256 byte boundary in memory.

The DMA controller circuit is designed to provide for both cycle steal and burst modes, under software programmability. This feature allows for increased efficiency at high data rates. Regardless of the mode chosen, the eight most significant bits are latched, and the next sample is latched in the same manner. At this point, the DMA transfer will proceed in the specified mode. It is important to note that by first latching 16 bits and then requesting the bus, the bus bandwidth used in cycle steal mode is cut to one half of what it would otherwise have been.

Figure 13A:
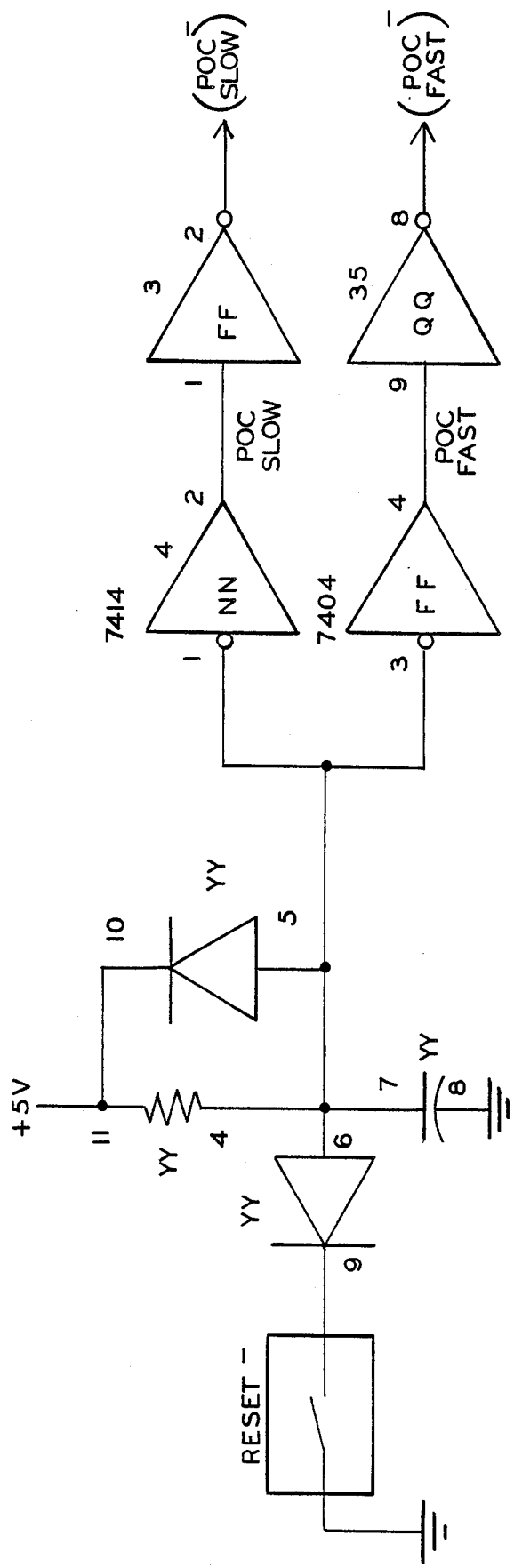
FIG. 13a is a schematic showing the 1.5 Volt local voltage source as used in the present invention.
Figure 13B:
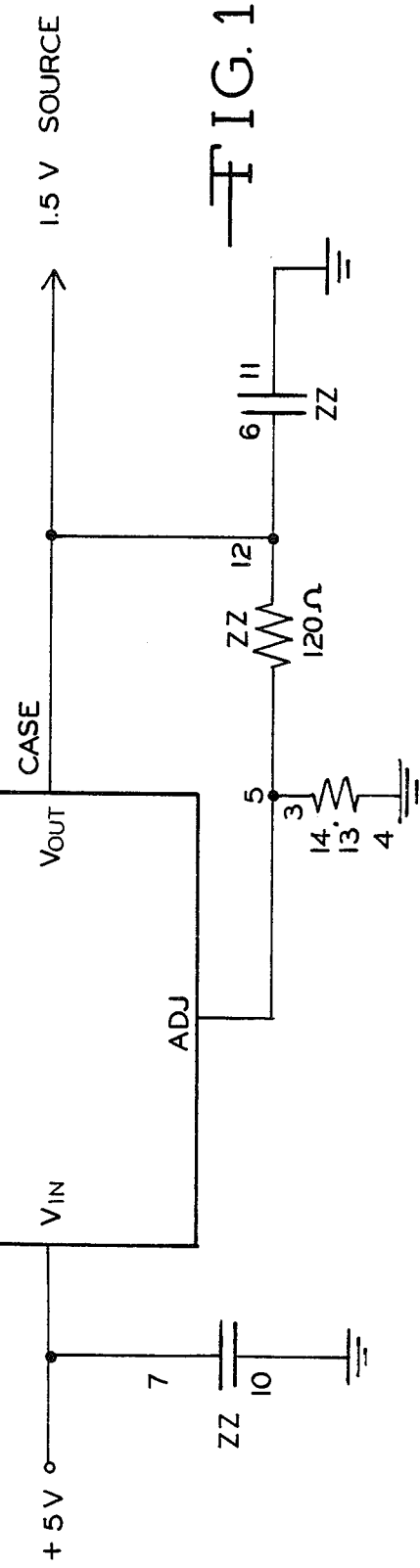
FIG. 13b is a schematic showing the Power-On Clear circuitry as used in the present invention.
Figure 14A:
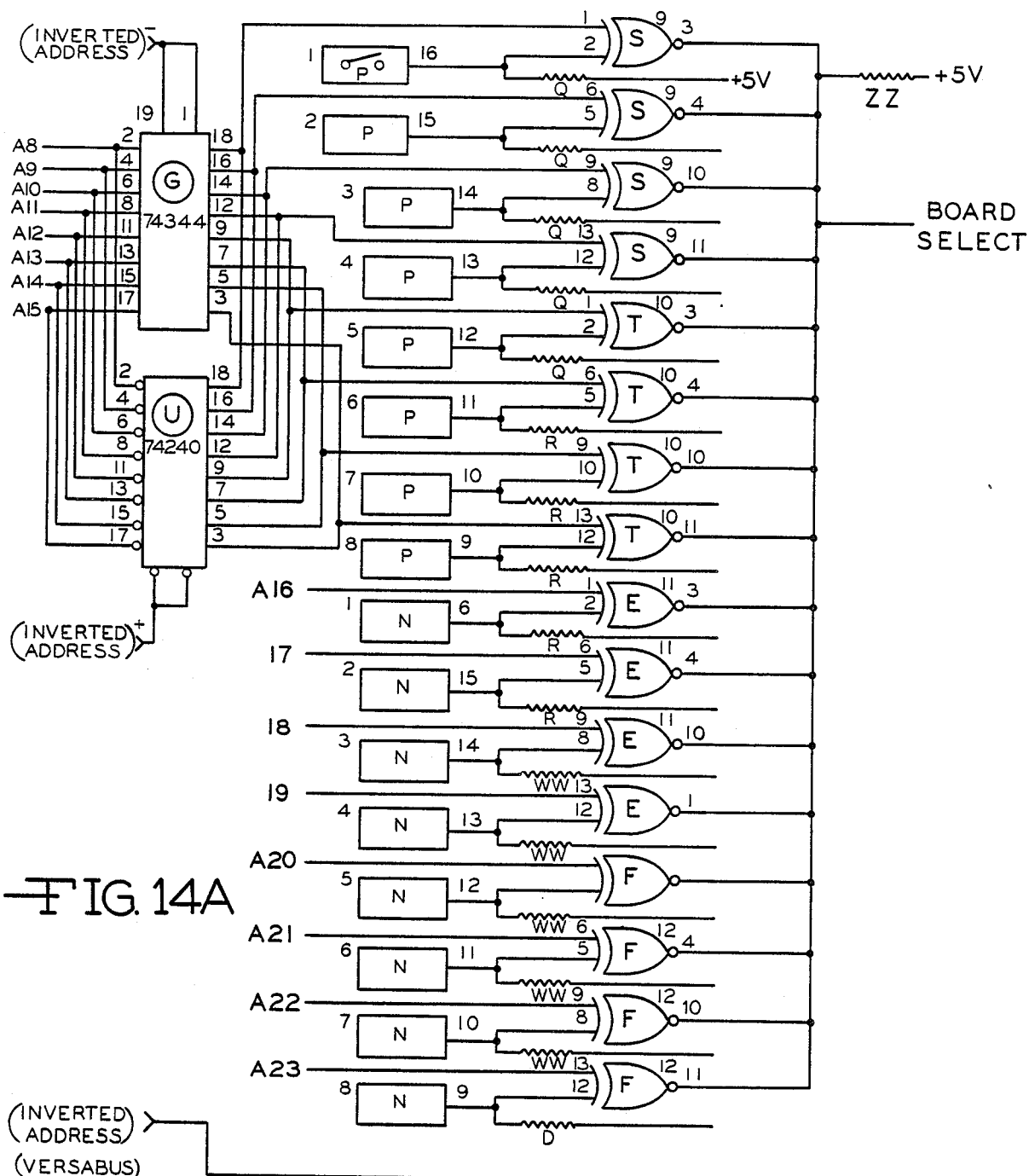
FIG. 14 is a schematic showing the board select logic as used in the present invention.
Figure 14B:
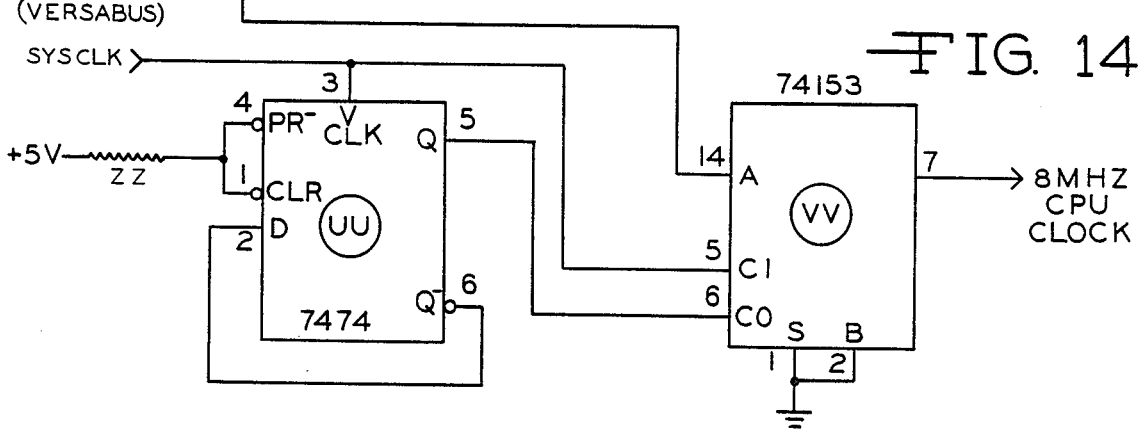

The remainder of the circuitry includes a 1.5 volt local power supply 48 (FIG. 13a), as required by the DMA control circuitry, and a dual speed power-on-clear circuit 50 (FIG. 13b) which included to ensure the circuit powers up in a predictable and stable manner.

With the circuitry in place, the device 10 is used to scan the object 12. The excited fluorescent intensity is determined using the highly efficient optical fiber faceplate 26 and the sensitive photomultiplier tube 30 without respect to the precise position of the laser beam on the target object. Such position is alternatively determined by the computer 32 which controls the three-dimensional scanner 22. The computer 32 then combines the X, Y coordinate spatial information with the intensity information to yield a high resolution wide-field image of the object 12.

Having thus described the invention in detail, it should be understood that various modifications and changes can be made in the apparatus without departing from the scope and content of the following claims.

What we claim is:

1. An apparatus for measuring the excited fluorescence of an object comprising:
   means for generating a coherent beam of light;
   a three dimensional scanner having means for securing such object in a fixed position, said scanner receiving and passing said coherent beam of light onto such fixed object in a desired pattern and at a desired rate, said scanner having X, Y coordinate scanning capability with simultaneous Z coordinate correction to cause said beam to have a topographical field of focus in the place of said object;
   means for controlling the pattern and rate at which said beam of light is passed onto said object;
   an optical fiber member for gathering and directing the fluorescent light induced from said object by said beam of light and for attenuating any direct light received by said object;
   means for collecting and measuring the intensity of the fluorescent light received from said object; and,
   means for sequentially recording data regarding the intensity of the fluorescent light received from said object as a function of the location of said scanning beam of light on said object by said scanner.

2. The apparatus of claim 1 further including a means for filtering said fluorescent light emanating from said optical fiber member.

3. The apparatus of claim 1 further including a means for diffusing said fluorescent light emanating from said optical fiber member.

4. The apparatus of claim 1, further including means for producing a visual image of at least a portion of said object based upon said sequentially recorded data of the intensity of said transmitted light as a function of the location of said scanning beam of light on said object.

5. The apparatus of claim 1, which further includes a focusing lens interposed between said means for generating a coherent beam of light and said three dimensional scanner.

6. The apparatus of claim 5, which further includes a beam expander interposed between said means for generating a coherent beam of light and said focusing lens.

7. The apparatus of claim 6, which further includes an iris diaphram interposed between said beam expander and said focusing lens.

8. The apparatus of claim 1, wherein said means for diffusing said transmitted light comprises an open-ended hollow elongated member having a reflective interior surface.

9. The apparatus of claim 1, wherein said means for collecting and measuring the intensity of the light transmitted through said translucent object comprises a photomultiplier tube.

10. The apparatus of claim 1, wherein said means for predeterminately controlling the pattern and rate at which said beam of light is passed over said object is a programmable computer.

11. The apparatus of claim 1, wherein said means for sequentially recording data is a programmable computer.

12. An apparatus for measuring the excited fluorescence of an object having a binding fluorescent dye application comprising:
means for generating a coherent beam of light;
means for expanding said coherent beam of light;
means for focusing said expanded beam of light;
a three dimensional scanner having means for securing such object in a fixed position, said scanner receiving and passing said focused beam of light over such fixed object in a selected pattern and at a selected rate, said scanner having X, Y coordinate scanning capability with simultaneous Z coordinate correction to cause said focused beam of light to have a topographical field of focus in the plane of said object;
means for controlling the pattern and rate at which said beam of light is passed through said translucent object;
a biased cut optical fiber faceplate for receiving and directing the fluorescent light transmitted from said object;
means for filtering said fluorescent light emanating from said fiber faceplate;
means for diffusing said filtered light;
means for collecting and measuring the intensity of the fluorescent light transmitted through said object; and
means for sequentially recording data regarding the intensity of the fluorescent light transmitted from said object as a function of the location of said scanning beam of light on said object.

13. The apparatus of claim 12, which further includes means for producing a visual image of at least a portion of said object based upon said sequentially recorded data as a function of the location of the fluorescent light transmitted from said object.

14. The apparatus of claim 12, which further includes an iris diaphram interposed between said means for expanding said beam of light and said means for focusing said expanded beam of light.

15. The apparatus of claim 12, wherein said means for generating a coherent beam of light is a laser.

16. The apparatus of claim 12, wherein said means for expanding said beam of light is a variable beam expander.

17. The apparatus of claim 12, wherein said means for controlling the pattern and rate at which said beam of light is passed over said object is a programmable computer.

18. The apparatus of claim 12, wherein said means for diffusing said fluorescent light is an open-ended hollow elongated member having a reflective interior surface.

19. The apparatus of claim 12, wherein said means for collecting and measuring the intensity of the fluorescent light transmitted from said translucent object is a photomultiplier tube.

20. The apparatus of claim 12, wherein the means for sequentially recording data is a programmable computer.

21. An apparatus for measuring the excited fluorescence of an object having a finding fluorescent dye application comprising;
a laser for generating a coherent beam of light at a specified wavelength with the range of 350 to 540 nanometers;
a variable beam expander for expanding said coherent beam of light;
a focusing lens to focus said expanded beam of light;
a three dimensional scanner having means for securing such object in a fixed position, said scanner receiving and passing said focused beam of light over such fixed object in a selected pattern and at a selected rate, said scanner having X, Y coordinate scanning capability with simultaneous Z coordinate correction to cause said focused beam of light to have a topographical field of focus in the plane of said object;
means for controlling the pattern and rate at which said focused beam of light is passed over said object;
a biased cut optical fiber faceplate for receiving and directing the fluorescent light transmitted from said object;
filter means for receiving said fluorescent light from said fiber optic bundle and removing unwanted light input;
diffusion means for diffusing said filtered light;
a photomultiplier for measuring the intensity of the fluorescent light transmitted and received from said diffusion means; and,
means for sequentially recording data regarding the intensity of the fluorescent light transmitted from said object as a function of the location of said scanning beam of light on said object.

22. The apparatus of claim 21, wherein said means for controlling the pattern and the rate at which said focused beam of light is passed over said object is a programmable computer.

23. The apparatus of claim 21, wherein said means for sequentially recording data is a programmable computer.

24. The apparatus of claim 21, wherein said diffusion means is an open-ended hollow elongated member having a reflective interior surface.

25. The apparatus of claim 21, which further includes an iris diaphragm interposed between said beam expander and said focusing lens.

26. The apparatus of claim 21, which further includes means for producing a visual image of at least a portion of said object based upon said sequentially recorded data as a function of the location of the fluorescent light transmitted from said object.

* * * * *